United States Patent [19]

Jack

[11] 4,216,768
[45] Aug. 12, 1980

[54] DEVICE FOR INHALING POWDERED SUBSTANCE

[76] Inventor: Whitfield Jack, 423 Front St., Key West, Fla. 33040

[21] Appl. No.: 889,413

[22] Filed: Mar. 23, 1978

[51] Int. Cl.² .......................................... A61M 15/00
[52] U.S. Cl. .............................. 128/203.15; 128/266
[58] Field of Search ...................... 128/172, 173.3, 185, 128/187, 206, 213, 222, 265, 266

[56] References Cited

U.S. PATENT DOCUMENTS

| 214,617 | 4/1879 | Brown | 128/222 X |
|---|---|---|---|
| 620,792 | 3/1899 | Middleton | 128/222 |
| 1,200,490 | 10/1916 | Hall | 128/222 |

FOREIGN PATENT DOCUMENTS 17663  4/1882  Fed. Rep. of Germany .......... 128/222

Primary Examiner—Henry J. Recla
Attorney, Agent, or Firm—Robert L. Slater, Jr.

[57] ABSTRACT

A device for administering to a patient by inhaling through a nostril a measured quantity of powdered substance comprised of a concave spoon having a first end of a hollow tube attached thereto, the tube interior communicating to the spoon concavity, a flange having an aperture there through, the second end of the hollow tube attached to the flange and the hollow interior of the tube opening through the flange aperture.

2 Claims, 2 Drawing Figures

DEVICE FOR INHALING POWDERED SUBSTANCE

FIELD OF THE INVENTION

The present invention relates to a device for administering measured quantities of powdered medicinals, snuff or the like by means of inhalation through the patient's or users nostril.

BACKGROUND OF THE INVENTION

Various medicinal materials as well as snuff and like substances are best administered to the patient, or user, in controlled quantities of fine powder inhaled through the nostril and placed in direct contact with the patient's upper respiratory system surfaces.

Various spray means have been devised to administer vaporized and atomized droplets of liquid medicinals through the patient's respiratory system by nostril inhalation of vapor or droplets. However, numerous medicinal materials useful for treating respiratory system discomfort or disease are best preserved and most effectively administered as fine powdered dust inhaled through the patient's nostrils. Simple effective means to administer dry powdered inhalant to the patient's respiratory surfaces has heretofore been lacking. Those powder inhalant devices that were available lacked simplicity of design and ease of use. Those dry powder inhaler devices heretofor described required several parts to be disassembled and then reassembled by the user to utilize the device.

There remained the need for a simple effective and inexpensive device to administer measured quantities of powdered substance by nasal inhalation.

Accordingly, one object of my invention is to provide a simple effective device for administering powdered inhalant material.

Another object of my invention is to provide a simple device for measuring a controlled quantity of dry powdered substance and administering the substance through nasal inhalation.

SUMMARY OF INVENTION

A device for administering a measured quantity of a powdered substance to a person by nasal inhalation comprised of a flange having an aperture there through for covering one nostril, a hollow tube the first end of which is connected to the flange, the hollow interior of the tube opening through the flange aperture, a concave spoon, the second end of the hollow tube being connected to the spoon, the hollow interior thereof opening into the spoon concavity, whereby measured quantities of powdered substances placed in the spoon concavity may be administered through a patient's nostril.

DESCRIPTION OF PREFERRED EMBODIMENT OF INVENTION

Figure 1:
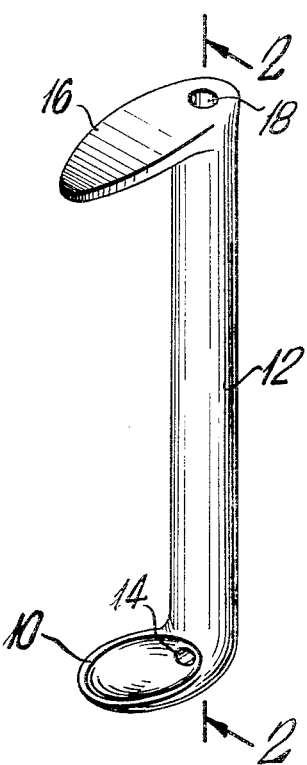
FIG. 1 is a perspective view of a preferred embodiment of my invention.

A preferred embodiment of my invention comprising an instrument for administering a measured quantity of powdered substance to a patient through one nostril is illustrated in FIG. 1.

A hollow spoon 10 is mounted to the lower end of an elongated tube 12. The tube 12 is provided with an axial channel or opening 14 passing there through. The lower end of the axial opening 14 of the tube connects to the concave hollow spoon 10.

A flange 16 is mounted to the upper end of the tube 12. An aperture 18 in the upper surface of the flange 16 connects to the axial channel 14 of the elongated tube. Thus, an open channel between the interior or concave portion of the spoon 10 is provided which connects through the elongated tube 12 and into the flange aperture 18.

Figure 2:
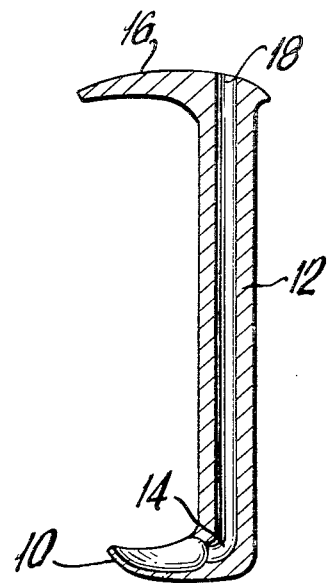
FIG. 2 is a cross section elevation view of the embodiment of my invention shown in FIG. 1.

FIG. 2, a vertical cross section view of the instrument, clearly illustrates the arrangement of the air passage and component parts of the invention described above. To use the device a patient places the flange 16 over one nostril, holding the other nostril closed. The patient then inhales, sucking through his nostril, whatever powdered substance had previously been placed in the concave spoon 10.

the spoon 10 has a measured volume within its concave cavity within which powdered inhalant substances may be placed. The volume of the spoon concavity may conveniently be for instance, one-eighth or one-fourth cubic centimeter. Thus, the medicinal dosage can be readily judged by leveling the powdered inhalant with the rim of the hollow spoon.

My inhalant administration device may be preferrably of a corrosion resistant metal, such as aluminum, stainless steel, silver or other metal. The metal surface may be plated to increase corrosion resistance. The device may also be conveniently made of plastic or other easily molded or machined material.

The foregoing specification and description is illustrative of my invention, the scope of which is defined in the following claims.

What is claimed is:

1. A device for administering powdered medicinal substances by inhaling through a nostril comprised of planar flange means adatped to occlude a person's nostril opening having an aperture there through, a concave spoon, the spoon having a predetermined volume, a hollow tube, the tube having a first end mounted to the spoon, the hollow interior of the tube opening into the spoon concavity and the second end of the hollow tube mounted to the flange means, the hollow interior of the tube opening through the aperture in the flange means, whereby when the flange means is placed over a person's nostril, powdered substance placed in the spoon concavity may be readily inhaled through the hollow tube into the patient's nostril.

2. A device for administering to a person by inhaling through a nostril a measured quantity of powdered substance comprising and elongated hollow tube, the tube having an upper end and a lower end, an extended planar flange, means having a planar area adapted to occlude a person's nostril opening, the upper end of the tube mounted to the flange means, the hollow interior of tube opening extending through the flange means and opening on the upper surface thereof, a concave spoon, the lower end of the tube mounted onto the spoon and the hollow interior of the tube opening into the concavity of the spoon, whereby measured quantities of powdered substances placed in the spoon concavity may be administered directly through a person's nostril by placing the upper surface of the flange against a nostril which then closes the covered nostril except for the hollows tube opening when the person inhales.

* * * * *